United States Patent
Bardorz et al.

(10) Patent No.: US 12,109,342 B2
(45) Date of Patent: Oct. 8, 2024

(54) MEDICAL DEVICE WITH TIME-CONTROLLED START FUNCTION

(71) Applicant: FRESENIUS MEDICAL CARE DEUTSCHLAND GMBH, Bad Homburg (DE)

(72) Inventors: Christoph Bardorz, Rottendorf (DE); Matthias Pfeuffer, Ebenhausen (DE); Thomas Schmitt, Dittelbrunn (DE); Carsten Mueller, Euerbach (DE)

(73) Assignee: FRESENIUS MEDICAL CARE DEUTSCH AND GMBH, Bad Homburg (DE)

( * ) Notice: Subject to any disclaimer, the term of this patent is extended or adjusted under 35 U.S.C. 154(b) by 84 days.

(21) Appl. No.: 18/076,629

(22) Filed: Dec. 7, 2022

(65) Prior Publication Data
US 2023/0173151 A1 Jun. 8, 2023

Related U.S. Application Data (62) Division of application No. 16/303,576, filed as application No. PCT/EP2017/062094 on May 19, 2017, now Pat. No. 11,571,500.

(30) Foreign Application Priority Data

May 20, 2016 (DE) .................... 10 2016 006 090.5

(51) Int. Cl.
*A61M 1/14* (2006.01)
*A61L 2/24* (2006.01)
*G16H 40/60* (2018.01)

(52) U.S. Cl.
CPC ............ *A61M 1/14* (2013.01); *A61L 2202/24* (2013.01)

(58) Field of Classification Search
CPC ....... A61M 1/14; A61L 2202/24; G16H 40/60
See application file for complete search history.

(56) References Cited

U.S. PATENT DOCUMENTS

| 4,399,030 | A | 8/1983 | Hlavinka et al. |
| 4,695,385 | A | 9/1987 | Boag |
| 4,789,467 | A | 12/1988 | Lindsay et al. |
| 5,472,614 | A | 12/1995 | Rossi |
| H1658 | H | 7/1997 | Love et al. |
| 5,863,421 | A | 1/1999 | Peter, Jr. et al. |
| 2012/0138533 | A1 | 6/2012 | Curtis et al. |
| 2013/0201222 | A1 | 8/2013 | Doyle et al. |

FOREIGN PATENT DOCUMENTS

| CN | 1429629 | 7/2003 |
| CN | 101175514 | 5/2008 |
| CN | 203749392 | 8/2014 |
| DE | 102009054415 | 7/2011 |
| EP | 0831945 | 5/2005 |
| WO | WO 96/24396 | 8/1996 |
| WO | WO 96/40317 | 12/1996 |

*Primary Examiner* — Kevin Joyner
(74) *Attorney, Agent, or Firm* — Jacobson Holman PLLC (57) ABSTRACT

A medical device having a time-controlled start function and a control unit, which enables user-friendly operation of the medical device, is described. The medical device has a control unit, which is equipped for automatic start-up of the medical device at a predetermined point in time and for checking on whether, after start-up of the medical device, a predetermined event has occurred, and has a display screen for display of information when the check reveals that the event has not occurred. Furthermore, a corresponding process for user-friendly operation is described.

16 Claims, 5 Drawing Sheets

MEDICAL DEVICE WITH TIME-CONTROLLED START FUNCTION

BACKGROUND OF THE INVENTION

1. Field of the Invention

The invention relates to a medical device having a time-controlled start function and a control unit, which permits a user-friendly operation of the medical device.

2. Description of Related Art

Medical devices regularly require one or more actions that must be carried out before treatment of a patient can begin. To reduce the workload for the operator of the machine or to permit good utilization of equipment, medical devices have a time-controlled start function (auto-on).

After a predetermined period of time has elapsed or at a predetermined point in time, for example, a certain time of day, the machine starts automatically and automatically carries out at least one action. Automatic here is to be understood to mean that this action takes place without interaction by an operator.

Such an auto-on function is known, for example, for hemodialysis machines in which before the treatment, the liquid system through which water and/or dialysate flows during the treatment (hydraulic system) is cleaned.

SUMMARY OF THE INVENTION

This action may involve, for example, a cleaning process with which a liquid circulation of a hemodialysis machine can be cleaned before the treatment. Such a process is described, for example, in U.S. Pat. No. 4,789,467 A.

It has been found that this auto-on function can be simplified with regard to use.

The object is therefore to supplement the auto-on function with regard to user friendliness.

This object is achieved by means of a medical device and/or a process according to the independent patent claims. The dependent patent claims describe embodiment devices of the inventive device and/or of the inventive process. This object can also be achieved by means of a digital memory medium, by means of a computer program product and by means of a computer program, which imparts to the medical device the functionality of the patent claims when installed in a medical device.

The medical device may have a control unit, which is equipped for automatic starting of the medical device at a predetermined point in time and for checking, after a start of the medical device, to ascertain whether a predetermined event has occurred. Furthermore, the medical device may have a display screen for display of information if the check reveals that the event has not occurred.

The control unit may be configured, so that, as a result of the check, it causes the display screen to display the information without any further interaction on the part of a user. In other words the control unit may be configured to send a signal to display the information to the display and the information can be displayed without handling by a user. This automatic display can, but need not necessarily in all cases, be displayed on a surface of the display screen, which is presented to the user on start-up of the device immediately or without further interaction on the part of the user. The medical device may be configured, so that other messages and/or warnings and/or alarm messages are displayed to more or less cover the information. The medical device may be configured, so that these other messages and/or warnings and/or alarm messages must first be removed by the user before the information is automatically visible. This removal may include an acknowledgement and/or a shifting and/or a reduction in size of these other messages and/or warnings and/or alarm messages. However, the device may also be configured, so that, for display of information, it is not necessary to control a certain page in a menu structure for operation of the device. The system control and the display may be configured, so that the user must necessarily have the information displayed before he can begin a treatment with the medical device.

The event may be the start-up of the medical device at a predetermined point in time or control of an actuator or a sensor and/or the running of a predetermined process. This process may be a cleaning process, in particular a rinse process and/or a disinfection process and/or a hot-cleaning process. The control may also be part of such a process.

The medical device may have a time recording device for recording time information. The check may include a comparison of the point in time of start-up of the medical device by means of the time recording device, detected by means of the time recording device, with the predetermined point in time, and the display may take place when the time lies at least a predetermined amount after the predetermined point in time.

The medical device may be configured, so that, when there is an auto-on, the predetermined point in time is set at the time of a new auto-on point in time. This makes it possible to ensure that comparing this time with the predetermined point in time allows detection of whether an auto-on event has been "missed."

The auto-on event may include predetermined process steps or one or more adjustable and/or selectable process steps, for example, one or more of the cleaning processes described above. Then the new auto-on point in time can be set only when the set and/or selected process steps have been carried out completely.

The predetermined or selectable process steps and/or processes may involve at least one process step from the group of the following process steps: heat disinfection, rinsing, degreasing, cold disinfection, integrated hot cleaning with a cool-down phase, system test. The individual process steps are known from the state of the art and are used in the dialysis machine 5008 from Fresenius Medical Care, for example. They are described below only briefly. Heat disinfection—in this case, disinfectant is heated and passed through line segments of the medical treatment machine. Rinsing is done only with water in a process similar to that of heat disinfection and the water can also be heated or, in another embodiment, this may be omitted. Therefore, residues of a previous disinfection, for example, can be rinsed out. Degreasing and cold disinfection also function like heat cleaning, but in this case different chemicals are added to the liquid and/or the liquid is not heated. In integrated heat cleaning, the liquid heated outside of the medical device can be sent through the medical device. A system test may include one or more steps, by means of which the functionality of the device is tested. These steps may include checking the sensors and/or the actuators of the device or a leakage test on the line system or functioning of the electronic system of the device.

The medical device may have a memory for storing event information when the event has occurred and the check may also include readout of the event information.

The check may include a comparison of the time information in start-up of the device with the predetermined point in time and, if the current time information occurs later than the predetermined point in time, it may include readout of the event information.

The medical device may have a sensor, in particular a conductivity sensor, a pressure sensor, a temperature sensor for detecting a property of a liquid in the medical device and the check may include a comparison of the detected property with a preset value.

The medical device may be a device for a blood treatment, in particular an extracorporeal blood treatment device and/or a dialysis machine. The device may be a hemodialysis machine, a peritoneal dialysis machine, a plasmapheresis machine or a liver assist therapy device.

The information shown on the display screen may include an interactive input element, which, on activation by the user, causes the control unit to start a process, in particular a cleaning process. The cleaning process may be one of the cleaning processes described above.

The control unit may be configured to display a selection of one or more options for setting the medical device by the user and the display screen. This display of options may include the representation of the information described above as a result of the check.

A first option may include a first cleaning process and a second option may include a second cleaning process, wherein the duration of the first cleaning process is greater than the duration of the second cleaning process.

The medical device may have a user interface for turning the check on and off. When the check is turned off, at least one process can be carried out automatically after starting the device. The automatically executed process may be a process which is saved in a memory in the device as a process to be carried out automatically in the event of an automatic start-up of the device for the predetermined process.

One process for operating the medical device in a preparatory mode may include the following steps:

After a start-up of the medical device, a check for whether a predetermined event has occurred, wherein the medical device is equipped for automatic start-up at a predetermined point in time and display of information when the check has revealed that the event has not occurred.

Furthermore, the check may include a comparison of a start-up time with the predetermined point in time.

A digital memory medium and/or a computer program product can impart functionality to the medical device according to the process, as described in the previous paragraphs, when installed in a medical device.

DETAILED DESCRIPTION OF THE PREFERRED EMBODIMENTS

With reference to the figures, embodiments according to the invention are described below, wherein means that have the same functional effect are referred to using the same reference numerals.

In all the embodiments, the use of the term "may be" and/or "may have," etc. are to be understood as synonymous with "is in particular" and/or "has in particular," etc. and/or should explain an additional embodiment according to the invention. Embodiments according to the invention may have one or more of the features defined above or below in any combination as long as such a combination is not recognizably technically impossible for a skilled person.

Whenever numerical words are cited herein, the skilled person should understand them to be a statement of a lower numerical limit. If this does not lead to a recognizable contradiction for the skilled person, and therefore the skilled person will always infer "at least one" when the specification is "one." This understanding is also included in the present invention along with the interpretation that a numerical word such as "one" can be interpreted alternatively to mean "exactly one," whenever this is technically feasible for the skilled person. Both of them are covered by the present invention and apply to all numerical words used herein.

Figure 1:
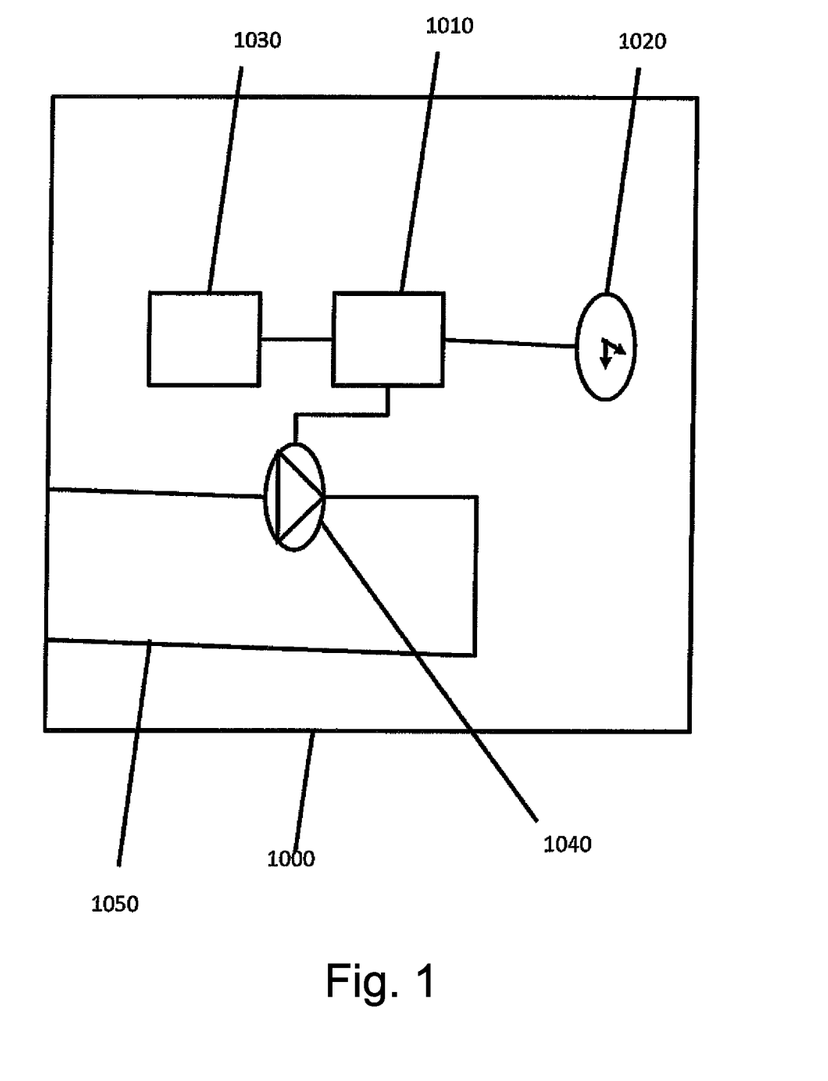
FIG. 1 shows a first embodiment of the medical device.

FIG. 1 shows a schematic diagram of a medical device 1000 on the example of a fluid-carrying medical device 1000. The medical device 1000 has a control unit 1010, a timekeeping device 1020 and a display screen 1030. The control until 1010 is equipped for automatic start-up of the medical device 1000 at a predetermined point in time and for checking on whether a predetermined event has occurred. If this check reveals that the event has not occurred, then the control unit is configured to send a signal to the display screen 1030 for display of information. The display of information on the display 1030 may take place automatically without any further action on the part of the user. This may also be understood to include the situation, wherein the menu guide of the medical device 1000 is configured so that the user must necessarily have received a display before he can carry out a treatment on a patient.

The control unit 1010 may have a processor, a memory and a communication bus. Information can be saved in the memory. When this information is reviewed by a software routine carried out in the processor, the control unit 1010 can ascertain whether the predetermined event has taken place.

This check may be a comparison of a start time with a predetermined start time saved in the memory, for example. The system control can be configured to interpret the fact that the start time occurs at least a predetermined amount of time after the predetermined start time, so that the event has not yet taken place. The predetermined start time may be a time that can be determined by the user.

The predetermined amount may be an amount greater than 0 minutes, greater than 5 minutes, greater than 10 minutes or greater than 20 minutes. It is therefore possible to achieve the result that the starting point in time is not compared directly but instead a later point in time is compared. Therefore, actions which are to take place before the check according to the software being run can take place without having an influence on the result of the check. These actions may involve the run-up of the system, preceding tests or similar actions.

Alternatively or additionally, the system control may check at the time of start-up to ascertain whether the event has actually occurred between the predetermined point in time and the starting time. Therefore, when the event has occurred, an entry can be made in the memory, and the check may include readout of the memory entry by the control unit 1010. If the readout of the memory entry gives the result that the event has not occurred, then the control unit 1010 can send a signal to the display screen 1030 to display the information.

The occurrence of the event may include the start of a process and/or a process step or a complete sequence of a process step and/or a process.

The event may include control of an actuator 1040 or a sensor 1040. The control may serve to carry out a predetermined process in the medical device or to check the functionality of a part such as an actuator 1040 or a sensor 1040. The event may include a cleaning process, in particular a rinsing process and/or a disinfection process and/or a heat-cleaning process. The cleaning process may include heating of a liquid or a supply of a hot liquid from the outside, and may include a hot rinse process or a heat disinfection process. If the term "hot" is to be used, it should refer to at least 50° C., preferably 80° C., and the liquid for rinsing or cleaning may be water and/or RO water. The event may include a check or calibration of a sensor 1040. To carry out the process, the medical device 1000 may have a pump 1040 and a liquid system 1050, wherein the pump 1040 can be controlled by the control unit 2010 in such a way that flow of a liquid through the liquid system 1050 is generated. The sensor 1040 may have a conductivity sensor, a pressure sensor and/or a temperature sensor, by means of which the condition of a liquid in the liquid system 1050 can be determined for evaluating the status of the liquid or for evaluating the functionality of the sensor 1040.

The timekeeping device 1020 may be a quartz oscillator or a clock, for example. The signal of the timer 1020 can be transmitted to the control unit 1010, and the time information can be processed in the control unit 1010 in such a way that the medical device 1000 is started in the sense of an auto-on function according to time information saved in the memory, for example. The start-up may include automatic starting of the event, for example.

The term "processor" is not limited here to a single physical processor but instead the processor may also include a multi-core processor or some other type of processors or processor components linked together. The memory may be a volatile memory and/or a nonvolatile memory or a combination of same. The memories and processors may be set up remotely, i.e., for example, on a central server, which is not physically connected to a treatment module of the medical device 1000. The databus can serve to exchange data between the memory and processor. Recording whether or not an event has occurred may include automatic filing of the corresponding information in the memory. The term "filing" is to be understood to mean that non-filing is also included. The sensor device may thus read out a certain memory entry, and if the event has not occurred, this memory entry will be different from what it would be if the event had occurred. The control unit may have the physical modules of a computer, with which those skilled in the art are familiar and which are required in order to allow a program to run and thus to control a medical device. In addition to the processor, memory and communication bus mentioned above, such modules may also include interfaces to the devices to be controlled, such as actuators, sensors, display, hardwired and wireless communication and the like.

The display screen 1030 can provide the information, for example, on a graphical user interface by means of lamps, by means of acoustic signals or other display devices. The display screen 1030 may also include an interactive device such as a touchscreen and/or one or more buttons. Due to the interactive device the operator can send at least one instruction to the control unit 1010 in activation and send it for further processing by the control unit 1010. The further processing may involve control signals to actuators and/or to the sensors of the medical device and/or processes that are complex in the implementation.

Figure 2:
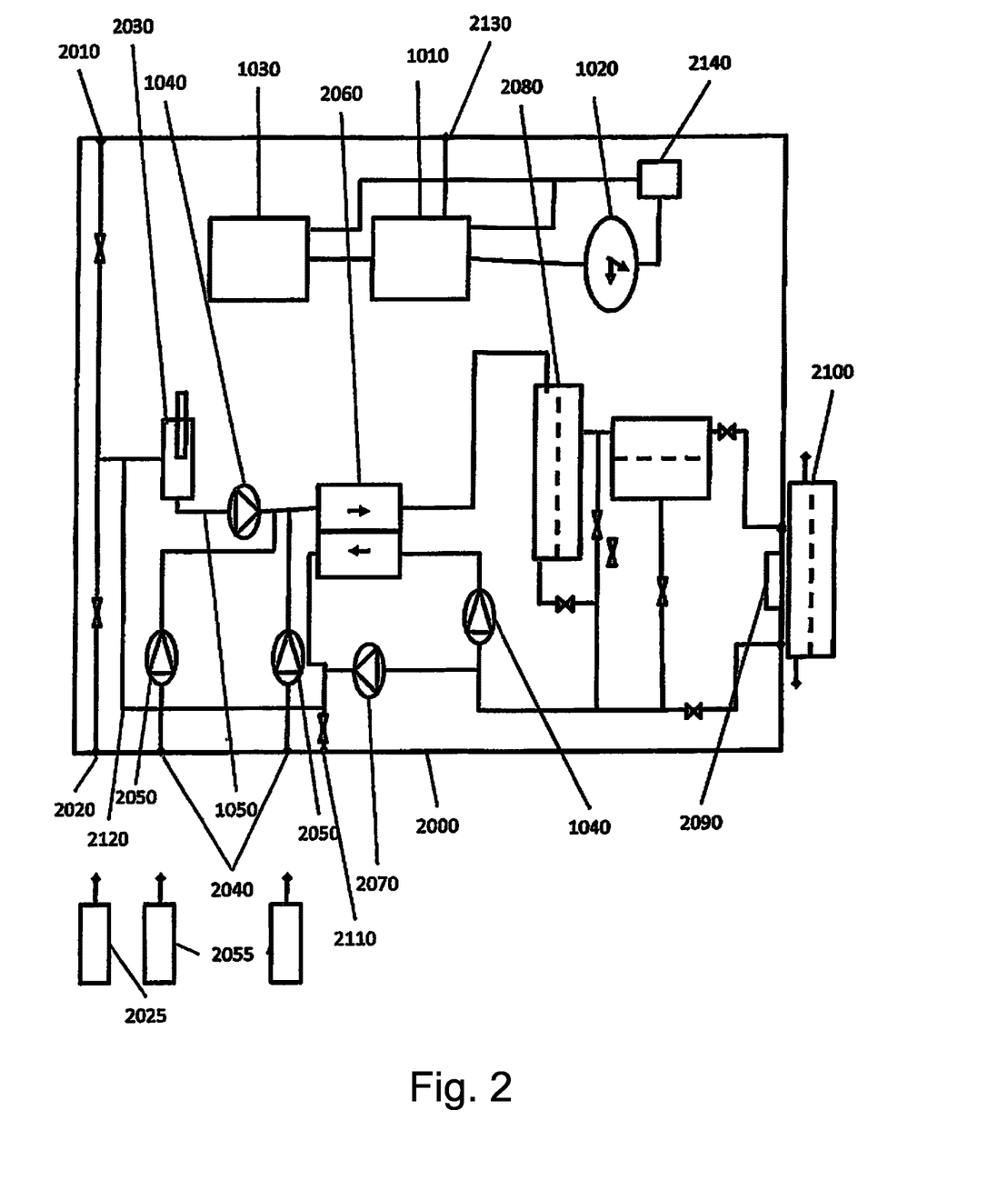
FIG. 2 shows a dialysis machine as an embodiment of the medical device.

The medical device 1000 may be a hemodialysis machine 2000, as illustrated in FIG. 2. The action described here is not limited to the hemodialysis machine 2000 of FIG. 2, but instead may be used with any hemodialysis machine and/or any medical device and/or dialysis machine with an auto-on function, as will be apparent to those skilled in the art. The term "hemodialysis machine" includes all forms of extracorporeal blood treatment machines, namely hemodiafiltration machines, plasma separation machines and ultrafiltration machines.

The hemodialysis machine 2000 may have a control unit 1010, a display screen 1030, and a timekeeping device 1020. Furthermore, the hemodialysis machine 2000 may have a pump 1040 for pumping a liquid through the liquid system 1050. The hemodialysis machine may have a water inlet 2010. The water inlet 2010 may be configured to be connected to a water source (not shown), for example, to an RO system of a central water supply system. Furthermore, the hemodialysis machine 2000 may also have a disinfectant connection 2020. The water and/or the disinfectant 2025 and/or a mixture of the two can be heated in a heating device 2030, for example, by carrying out a heat-cleaning process using water and/or disinfectant. Furthermore, the hemodialysis machine 2000 may have at least one concentrate connection 2040 and at least one concentrate pump 2050 for connection and pumping of concentrates 2055 for preparing the dialysate by mixing it with water from the water inlet 2010, a balancing system 2060, optionally with an ultrafiltration pump 2070, at least one sterile filter 2080. Furthermore, the hemodialysis machine 2000 may have a bypass 2090, through which liquid flowing through the liquid system can be circulated. Bypass 2090 can be used when the dialyzer 2100 is not connected to the liquid system 1050. Furthermore, the hemodialysis machine 2000 may have valves 20150, sterile filters 20160, accesses, short-circuit lines 20170, pumps, sensors. These are indicated schematically in FIG. 2, where those skilled in the art will understand how these elements can be arranged in order for them to be able to manifest their respective functionality.

For cleaning the hemodialysis machine 2000, water can be supplied to the liquid system 1050 via the inlet 2010 or dialysate can be supplied through the disinfection connection 2020. Then it can be heated using the heating device 2030 in a chamber and sent through the bypass 2090 to an outlet 2110 of the hemodialysis machine 2000. Furthermore, the liquid system 1050 of the hemodialysis machine 2000 may have a circulation section 2120. If the liquid is carried through this circulation section 2120, it is sent upstream to a region of the liquid system 1050. Therefore the liquid can circulate in the hemodialysis machine 2000, for example, in a circulation mode. This circulation mode may be part of a cleaning process.

The control unit 1010 of the hemodialysis machine 2000 may have at least the same functionality as the control unit 1010 of the medical device 1000 and may be constructed accordingly. A signal of the control unit 1010 can control the at least one actuator of the hemodialysis machine 2000 via signal lines (not shown) or may receive measured data from at least one sensor of the hemodialysis machine 2000.

The display screen 1010 of the hemodialysis machine 2000 and the timekeeping device 1020 may have at least the same functionality as the display screen 1010 of the hemodialysis machine 2000 and the timekeeping device 1020 of the medical device 1000 and may be constructed accordingly.

The hemodialysis machine 2000 may have a network connection 2130. The hemodialysis machine 2000 can be supplied with power via this network connection 2130, for example, for the system control, the display screen, the actuators or the sensors. The hemodialysis machine 2000 can be connected to a power source 2140. This power source 2140 may be a battery, which makes it possible to have some or all processes take place in the hemodialysis machine 2000, even without a connection via the network connection 2130 to supply it with power and/or allowing it to run.

Figure 3:
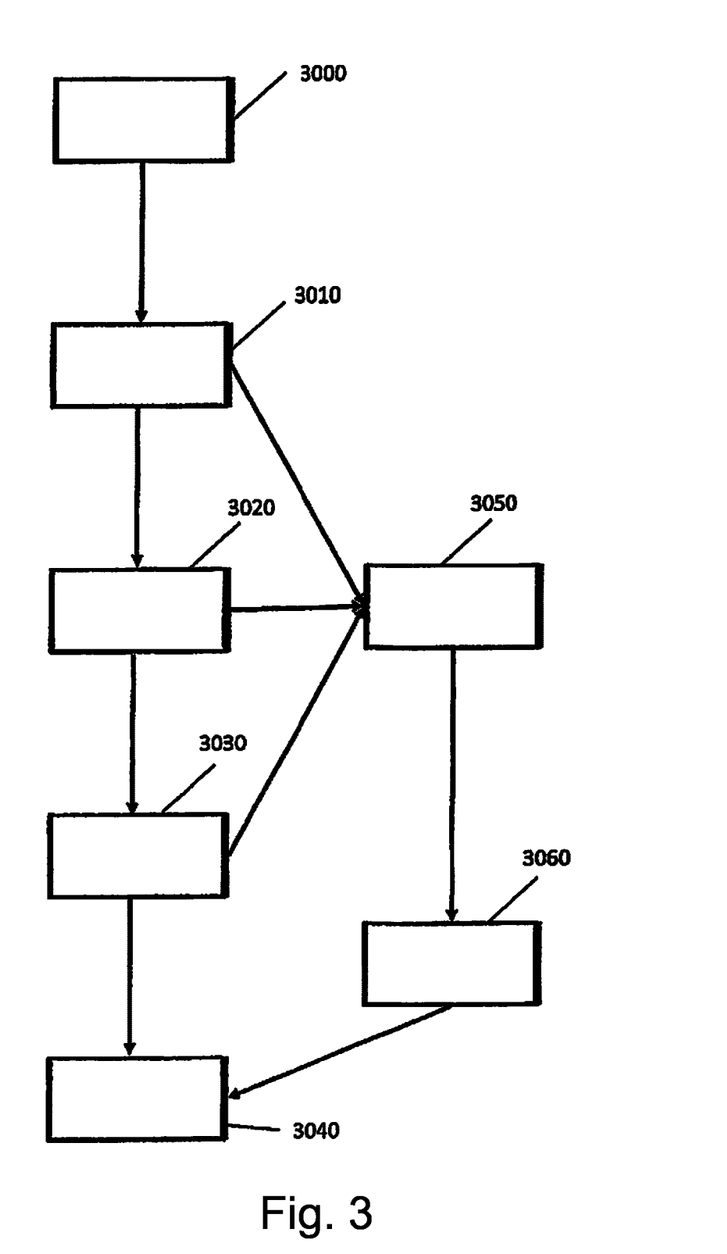
FIG. 3 shows a sequence of a process for starting operation of a medical device.

The control unit 1000 can carry out the check (FIG. 3). First, the auto-on function is activated 3000 by a user. In doing so, the user can ascertain at which point in time the medical device 1000 should be started. Furthermore, the user can determine which processes should take place automatically after auto-on. This time and these processes can be saved. At least one action, which runs automatically when the device is started by means of the auto-on function, can also be saved. Examples of these processes and actions are described above, although the present invention is not limited to those.

When the machine is started 3010, the control unit 1010 checks 3020 on the current time, comparing it with the saved auto-on time (predetermined time). If the current time is after the auto-on time or is after that time by a predetermined amount, then the system control 1010 recognizes 3030 that the event has not occurred and outputs 3040 information about the display screen 1030.

Alternatively or in addition to the recognition that the event has failed to occur on the basis of the comparison of the start time with the auto-on time (steps 3020 and/or 3030), the control unit 1010 can make 3050 an entry into a memory at start-up and/or occurrence of an event. This may take place, for example, by means of a flag or a memory entry at a dedicated memory location. If the medical device 1000 is started at a later point in time, the control unit 1010 then checks 3060 the memory entry, and if the memory entry does not indicate that the event has taken place, information about the display screen 1030 is output 3040.

If the check is additionally carried out according to steps 3050 and 3060, then the display can take place only when both or at least one of the two checks has shown that the event has not occurred.

Figure 4A:
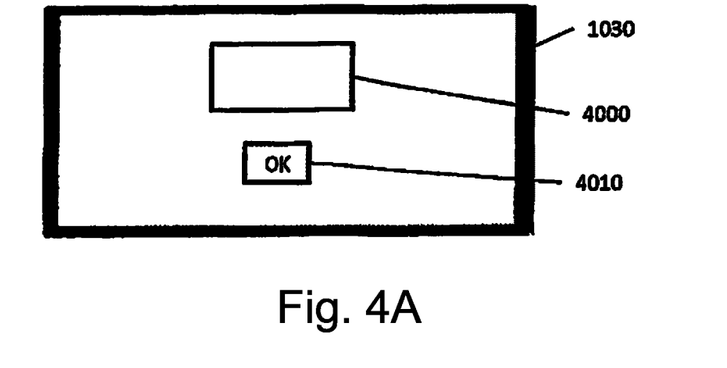
FIGS. 4A-4C show various embodiments of providing information for starting up operation of a medical device.

The information on the display screen 1030 may include a message 4000 that the event has not occurred (FIG. 4A). Furthermore, the information may include an acknowledgeable message 4010, for example, an OK message. By acknowledging, the medical device 1000 can be put in a ready-to-operate status in which a user can select additional processes. The information can also be acknowledged with two types of acknowledgement. The first type of acknowledgement may be a permanent acknowledgement, in which the message does not appear again, and the second type may be a transient acknowledgement, in which this information or some other information is displayed again after a predetermined period of time.

Figure 4B:
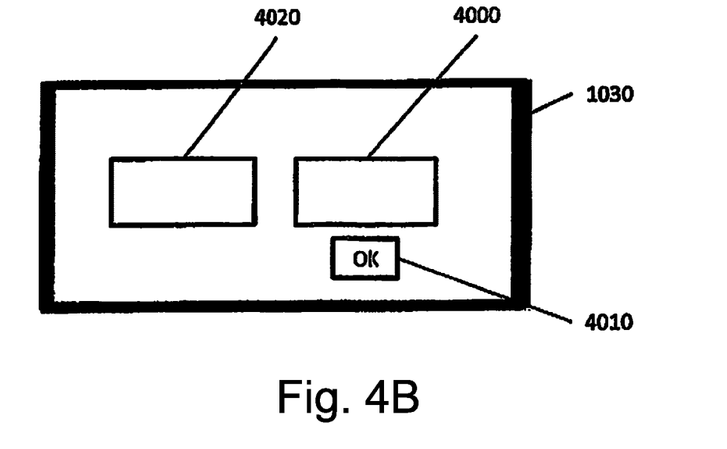

Alternatively or additionally, the information may include a selectable representation 4020 (option) (FIG. 4B). When this representation 4020 is selected, the user can choose the option that the event that has not occurred is to be carried out. The displayed information 4020 may include an interactive input element, which causes the control unit to start a process as an event on activation by the user. This process may comprise one or more of the actions described above, in particular a cleaning process. This action may be the action which has not taken place, for example, due to an auto-on start that has been missed.

Figure 4C:
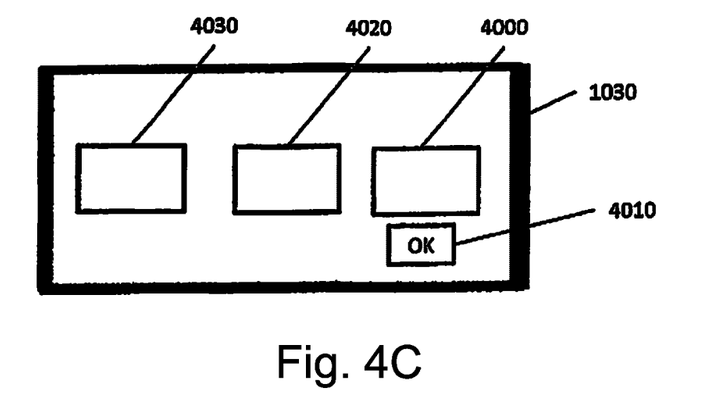

Alternatively or additionally, the information may include another selectable representation 4030 (additional option) (FIG. 4C). When this representation 4030 is selected, the user can choose the option of carrying out a predetermined event.

Due to the additional selectable representation 4030 in addition to the selectable representation 4020, the user is offered a choice of at least two options for the user to make a setting of the medical device on the display screen. A first option may include a first cleaning process and a second option may include a second cleaning process, wherein the duration of the first cleaning process is longer than the duration of the second cleaning process.

Figure 5:
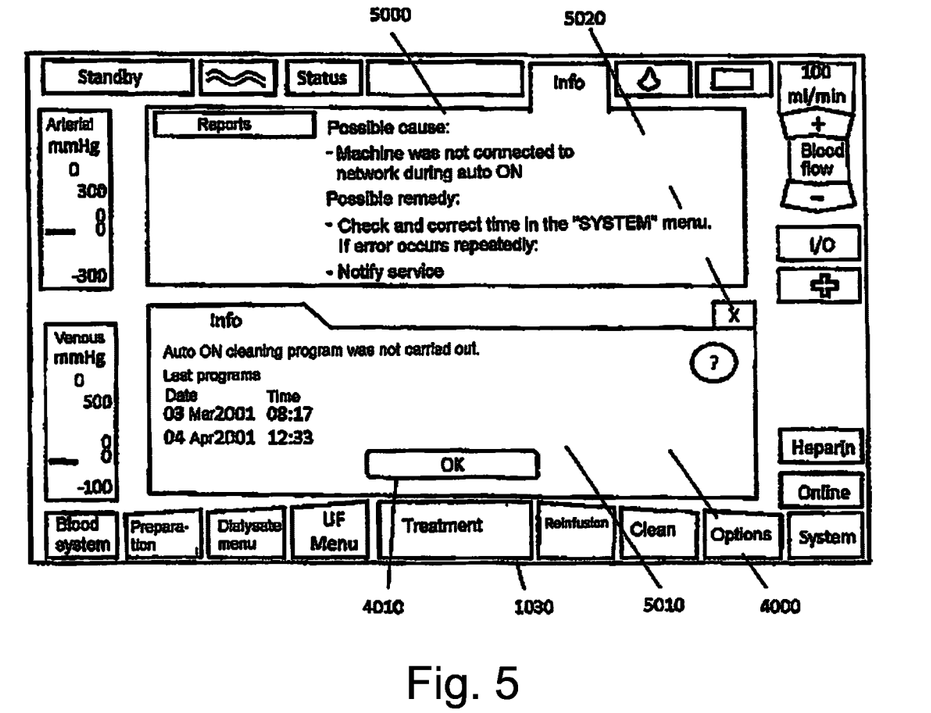
FIG. 5 shows another embodiment for providing information.

In another embodiment, which is represented schematically in FIG. 5, information 5000 informing the user about possible causes for the display of the information 4000 may be displayed on the display screen 1030 in addition to the information 4000 and the acknowledgeable information 4010. This additional information may instruct the user about possible actions the user himself may perform on the machine. The machine may also be configured, so that it saves at least the point in time of the most recent occurrence of an event and displays this point in time for the user when it is an event that was not carried out 5010 due to the non-occurrence of the automatic start. This can make it possible for the user to estimate whether it is necessary to actually carry out this event and/or process.

The acknowledgeable information 4010 may result in a permanent disappearance of the information. A second type of acknowledgeable information 5020 can also be displayed. With this type of information, the device is configured to display this information again after a predetermined period of time.

The embodiment disclosed in conjunction with the embodiment described on the basis of FIG. 5 can also be combined with any of the embodiments described on the basis of FIG. 4 or any embodiment according to the invention.

Furthermore, the medical device 1000 may have a user interface for activating and deactivating the check. The display screen 1030 or another input means may be this user interface. The display screen 1030 may be a touchscreen but additionally or alternatively, it may be any other type of information transfer, such as LEDs, lamps and as an interactive means, buttons, switches or the like.

The medical device may be configured to automatically carry out at least one process when the check is turned off after starting the device. The process carried out automatically may be a process which is saved in the medical device in a memory as a process to be carried out automatically in an automatic start of the device for the predetermined process.

Due to the check described above, it may be possible to operate the medical device more safely. For example, an auto-on start may be missed due to the fact that the machine is not connected to the network at the time of the auto-on start or there has been a power failure. Furthermore, there may also be a difference in the times of various timekeeping devices present in the device whose outputs are used to determine the current time and to determine the point in time when an event occurred. However, it may also be the case that the device is already running at the time of the auto-on and the event cannot occur.

The invention claimed is:

1. A medical device, comprising
a control unit equipped for automatically starting the medical device at a predetermined point in time and, after starting the medical device, checking on whether a predetermined, automatically carried-out event has occurred before starting the medical device, the control unit being configured to carry out the predetermined, automatically carried-out event, and a display screen for display of information when the check has shown that the event has not occurred.

2. The medical device according to claim 1, wherein the control unit is configured to send a signal to display the information to the display screen, and the information is displayed on the display screen without any action by a user.

3. The medical device according to claim 1, wherein the event includes starting the medical device at the predetermined point in time and/or controlling an actuator or a sensor and/or running a predetermined process.

4. The medical device according to claim 1, further comprising
a time recording device for recording the predetermined point in time,
wherein the check includes a comparison of a point in time of start-up of the mechanical device with the predetermined time, and the display occurs when the time occurs at least a predetermined amount after the predetermined time.

5. The medical device according to claim 1, further comprising
a memory for storing an event information when the event has occurred,
wherein the check includes readout of the event information.

6. The medical device according to claim 1, further comprising
a sensor for detecting a property of a liquid in the medical device,
wherein the check includes a comparison of the property thus detected with a preselected value.

7. The medical device according to claim 1, wherein the device is a device for a blood treatment.

8. The medical device according to claim 1, wherein the information displayed includes an interactive input element which causes the control unit, on activation by the user, to start a process.

9. The medical device according to claim 1, wherein the control unit is configured for display of a selection of at least one option for adjustment of the medical device by a user on the display.

10. The medical device according to claim 9, wherein a first option of the at least one operation is a first cleaning process and a second option of the at least one operation is a second cleaning process, wherein duration of the first cleaning process is longer than duration of the second cleaning process.

11. The medical device according to claim 1,
wherein the device has a user interface for turning the check on and off, and
wherein the device is configured to carry out at least one process automatically when the check is turned off after a start-up of the device.

12. The medical device according to claim 11, wherein the automatically executed process is a process which is saved for automatic execution in a memory of the device as a process to be carried out automatically with an automatic start of the device.

13. The medical device according to claim 1, wherein the event includes starting the medical device at the predetermined point in time and/or controlling an actuator or a sensor and/or running a predetermined process selected from the group consisting of a cleaning process, a rinsing process, and a disinfection process.

14. The medical device according to claim 1, further comprising
a conductivity sensor for detecting a property of a liquid in the medical device,
wherein the check includes a comparison of the property thus detected with a preselected value.

15. The medical device according to claim 1, wherein the device is a device for a blood treatment selected from the group consisting of an extracorporeal blood treatment machine and a dialysis machine.

16. The medical device according to claim 1, wherein the information displayed includes an interactive input element which causes the control unit, on activation by the user, to start a cleaning process.

* * * * *